United States Patent
Duvel et al.

(10) Patent No.: US 8,263,053 B2
(45) Date of Patent: Sep. 11, 2012

(54) HAIR TREATMENT COMPOSITIONS

(75) Inventors: Lane A. Duvel, Rockford, MI (US);
Ernest H. Brumbaugh, Rockford, MI (US); Matthew D. Berg, Grand Rapids, MI (US)

(73) Assignee: Access Business Group International, Ada, MI (US)

(*) Notice: Subject to any disclaimer, the term of this patent is extended or adjusted under 35 U.S.C. 154(b) by 1176 days.

(21) Appl. No.: 11/447,805

(22) Filed: Jun. 6, 2006

(65) Prior Publication Data

US 2007/0116653 A1    May 24, 2007

Related U.S. Application Data

(60) Provisional application No. 60/738,745, filed on Nov. 22, 2005.

(51) Int. Cl.
*A61K 8/00* (2006.01)
(52) U.S. Cl. .................................................. 424/70.1
(58) Field of Classification Search ................... None
See application file for complete search history.

(56) References Cited

U.S. PATENT DOCUMENTS

| | | | |
|---|---|---|---|
| 4,595,526 A * | 6/1986 | Lai | 510/423 |
| 4,983,383 A | 1/1991 | Maksimoski et al. | |
| 5,560,917 A * | 10/1996 | Cohen et al. | 424/401 |
| 5,661,118 A | 8/1997 | Cauwet et al. | |
| 5,683,684 A * | 11/1997 | Montastier et al. | 424/78.03 |
| 5,700,456 A | 12/1997 | Dubief et al. | |
| 5,830,481 A | 11/1998 | Cauwet-Martin et al. | |
| 5,939,077 A | 8/1999 | Saint-Leger et al. | |
| 6,110,450 A | 8/2000 | Bergmann | |
| 6,277,361 B1 | 8/2001 | Murray | |
| 6,379,659 B1 | 4/2002 | Ishida | |
| 6,403,111 B1 * | 6/2002 | Park et al. | 424/401 |
| 6,562,328 B2 | 5/2003 | Pereira | |
| 6,696,051 B2 | 2/2004 | Barbuzzi | |
| 6,730,331 B1 * | 5/2004 | Stoll | 424/728 |
| 6,805,856 B2 | 10/2004 | Wong | |
| 6,846,940 B2 | 1/2005 | Gaetani et al. | |
| 2003/0180237 A1 * | 9/2003 | Lersch et al. | 424/62 |
| 2004/0018162 A1 * | 1/2004 | Bimczok et al. | 424/70.2 |
| 2004/0029969 A1 * | 2/2004 | Blatt et al. | 514/565 |
| 2004/0171693 A1 * | 9/2004 | Gan et al. | 514/565 |

FOREIGN PATENT DOCUMENTS

| | | |
|---|---|---|
| JP | 06-287110 A | 10/1994 |
| JP | 09-278630 A | 10/1997 |
| JP | 11-139941 A | 5/1999 |
| JP | 11-222416 A | 8/1999 |
| JP | 2004143095 | 5/2004 |
| JP | 200662996 | 9/2006 |
| WO | 2005046629 A1 | 5/2005 |
| WO | 2007001843 A1 | 1/2007 |

OTHER PUBLICATIONS

CosmoCair C100 (Creatine-CP) for Hair Repair and Protection; 2002; bulletin; Centerchem, Inc., Norwalk, CT, USA.

* cited by examiner

*Primary Examiner* — Anand Desai
*Assistant Examiner* — Melissa Mercier
(74) *Attorney, Agent, or Firm* — Bryan Cave LLP

(57) ABSTRACT

The present invention relates to hair treatment compositions and methods. More particularly, the invention relates to hair treatment compositions comprising lipids and creatine. The hair treatment compositions of the present invention may be used to improve the tensile properties of hair, such as hair elasticity and strength.

9 Claims, 5 Drawing Sheets

HAIR TREATMENT COMPOSITIONS

CROSS-REFERENCE TO RELATED APPLICATIONS

This application claims the benefit of U.S. provisional patent application Ser. No. 60/738,745, filed Nov. 22, 2005, which is incorporated herein by reference.

FIELD OF THE INVENTION

The present invention relates to hair treatment compositions and methods of improving the tensile properties of hair using such compositions.

BACKGROUND OF THE INVENTION

It is well known that hair is routinely subjected to damaging and harsh agents. Examples of such agents include the chemicals found in hair sprays, gels, and coloring, bleaching, straightening, and curling formulations; the mechanical and heat energy applied during styling and/or hair drying, curling, or straightening; and the heat and stress imparted by exposure to the sun. Indeed, the harsh agents of everyday life often damage hair. Such damage may cause hair to break or split. In addition, such agents may cause hair to lose desired softness and appeal. That is, the above-mentioned agents and stresses that are applied to hair during everyday life often negatively impact the tensile properties of hair, such as hair elasticity and strength.

In view of the foregoing, there is a need for compositions that increase the tensile properties of hair.

SUMMARY OF THE INVENTION

One embodiment of the present invention is a hair treatment composition, which comprises (a) from about 0.01% to about 10.0% by weight relative to the total weight of the composition of a lipid and (b) from about 0.01% to about 10.0% by weight relative to the total weight of the composition of creatine.

Another embodiment of the present invention is a method for improving the tensile properties of hair. This method comprises applying to hair a composition comprising (a) from about 0.01% to about 10.0% by weight relative to the total weight of the composition of a lipid and (b) from about 0.01% to about 10.0% by weight relative to the total weight of the composition of creatine.

A further embodiment of the present invention is a hair treatment composition made by a process, which comprises combining from about 0.01% to about 10.0% by weight relative to the total weight of the composition of a lipid and from about 0.01% to about 10% by weight relative to the total weight of the composition of creatine to form the composition.

DETAILED DESCRIPTION OF THE INVENTION

Figure 1:
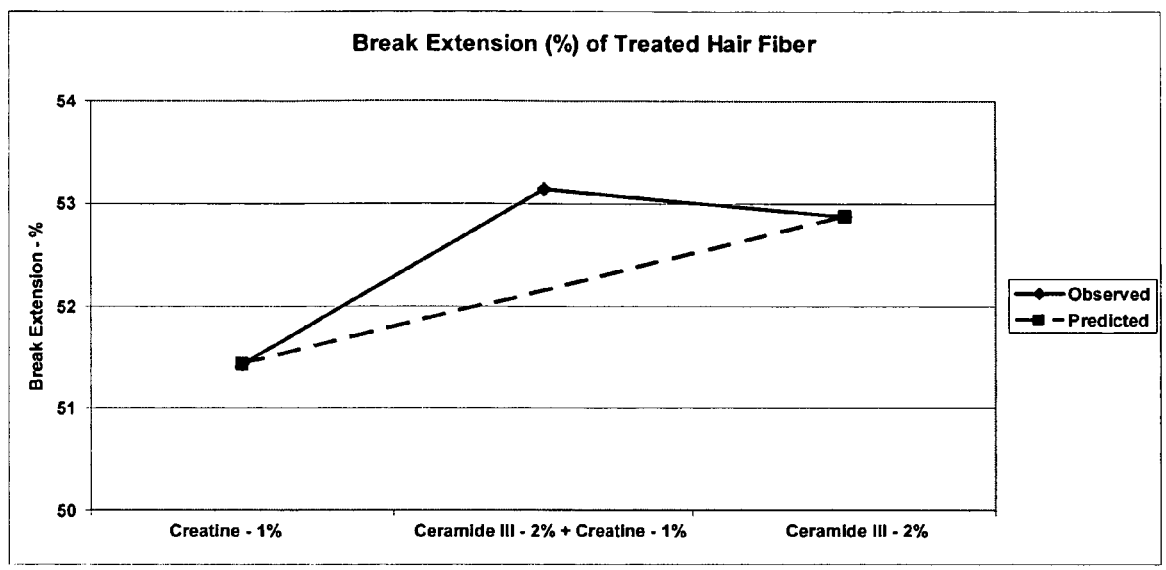
FIG. 1 is a line graph showing that hair treated with shampoo/conditioner formulations having both ceramide 3 and creatine (Group III) has superior Break Extension values compared to predicted values (which are based on the values observed for hair treated with the same shampoo/conditioner formulations that contained ceramide 3, but no creatine (Group I), and creatine, but no ceramide 3 (Group II)).

The present invention relates generally to hair treatment compositions. In one embodiment of the present invention, a hair treatment composition is provided that comprises (a) from about 0.01% to about 10.0% by weight relative to the total weight of the composition of a lipid and (b) from about 0.01% to about 10.0% by weight relative to the total weight of the composition of creatine. Preferably, the lipid and creatine are present in the composition at a molar ratio of between about 1:10-10:1. It is also preferred that the lipid and creatine are each present in the composition between about 0.01% and 3.0% by weight, based on the total weight of the composition. More preferably, the lipid and creatine are each present in the composition between about 1.0% and 3.0% by weight, based on the total weight of the composition.

As used herein, "creatine" refers to (α-Methylguanido) acetic acid N-Amidinosarcosine, and includes the phosphate form thereof, as well as derivatives, salts, and precursors thereof. Such creatine compounds are represented by the general structure below:

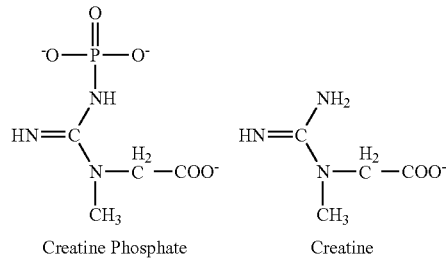

Creatine Phosphate     Creatine

In certain additional embodiments, the hair treatment compositions may further comprise other free amino acids (i.e., in addition to creatine). As used herein, the term "free amino acid" means that the amino acid is not covalently bonded to any other molecule by way of an amide bond. Still further, the compositions of the present invention may include creatine in combination with (i) other "free amino acids" and/or (ii)

proteins that comprise amino acid residues linked to one another by way of amide bonds (i.e., amino acids that define a protein).

The free amino acids that may, optionally, be used in the present invention may be either naturally or non-naturally occurring. As used herein, a "naturally occurring amino acid" is one that has the general core structure

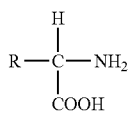

and that is synthesized in nature. A "non-naturally occurring amino acid" is a analog, derivative and/or enantiomer of a naturally occurring amino acid.

Non-limiting examples of naturally occurring amino acids that may be used in the present invention include alanine, arginine, asparagine, aspartic acid, carnitine, cysteine, glutamine, glutamic acid, glycine, histidine, isoleucine, leucine, lysine, methionine, phenylalanine, proline, serine, threonine, tryptophan, tyrosine, valine, and derivatives, analogs, and combinations thereof. The present invention includes dextrorotary (D) and levorotary (L) stereoisomers of such amino acids, as well as mixtures thereof, such as for example 50:50 mixtures of D- and L-amino acids.

The compositions of the present invention also include a lipid. As used herein, "lipid" means fatty acids and derivatives thereof, as well as substances related biosynthetically or functionally to such compounds. Non-limiting examples of lipids suitable for use in the compositions of the present invention include saturated fatty acids, unsaturated fatty acids, anteiso methyl-branched fatty acids, such as 18-methyl-eicosanoic acids, prostaglandins, monoglycerides, diglycerides, and triglycerides, phosphoglycerides, phospholipids, sphingolipids, steroids, and combinations thereof. Preferably, the lipid is a steroid, having a chemical scaffold represented by the following structure:

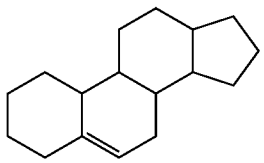

An example of a preferred steroid useful in the present invention is cholesterol. A non-limiting example of a cholesterol according to the present invention, $C_{27}H_{46}O$, has the general structure shown below:

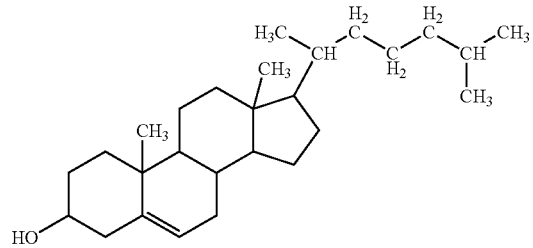

Another preferred example of a lipid useful in the present invention is a sphingolipid. In the present invention, sphingolipids include, for example, ceramides, such as ceramide 2, ceramide 3, glucosylceramides, and combinations thereof. The ceramides that may be used in the present invention may be naturally occurring or synthetic molecules, which correspond to the general formula:

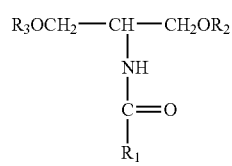

wherein:
$R_1$ is a saturated or unsaturated linear or branched alkyl radical derived from $C_{14}$-$C_{30}$ fatty acids, it being possible for this radical to be substituted with a hydroxyl group in the α-position or a hydroxyl group in the ω-position which is esterified with a saturated or unsaturated $C_{16}$-$C_{30}$ fatty acid;

$R_2$ is a hydrogen atom or a (glycosyl)$_n$, (galactosyl)$_m$ or sulphogalactosyl radical in which n is an integer ranging from 1 to 4 and m is an integer ranging from 1 to 8; and $R_3$ is a saturated or unsaturated $C_{15}$-$C_{26}$ hydrocarbon radical in the α-position, which may be substituted with one or more $C_1$-$C_{14}$ alkyl radicals. In the case of natural ceramides or glycoceramides, $R_3$ may also be a $C_{15}$-$C_{26}$ α-hydroxyalkyl radical, the hydroxyl group optionally being esterified with a $C_{16}$-$C_{30}$ α-hydroxyl acid.

In the present invention, one or more of the following ceramides may be used:

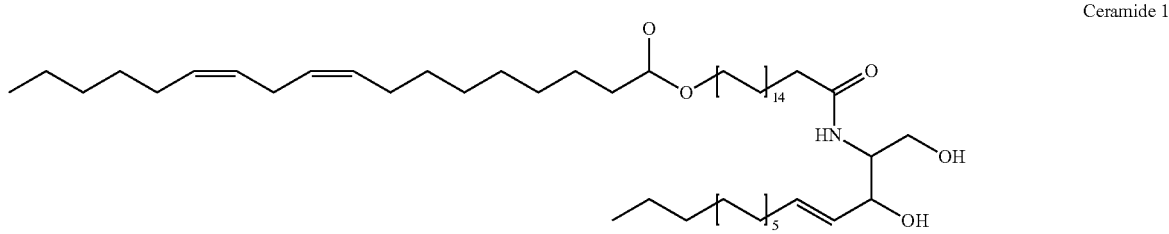

Ceramide 1

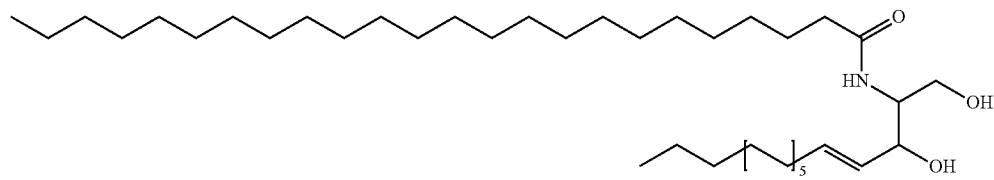

Ceramide 2

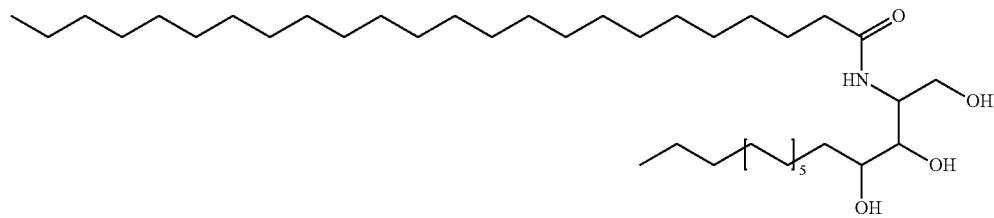

Ceramide 3

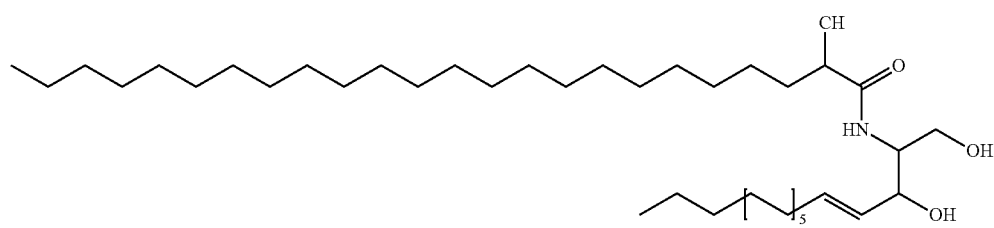

Ceramide 4

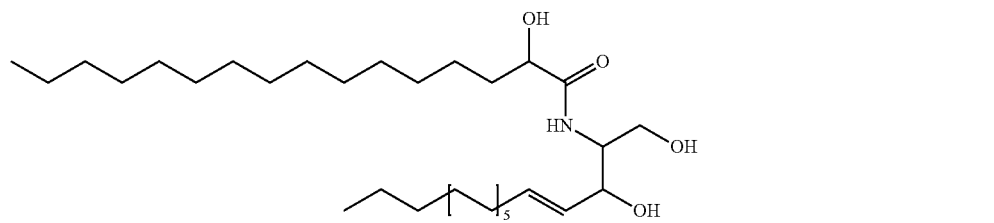

Ceramide 5

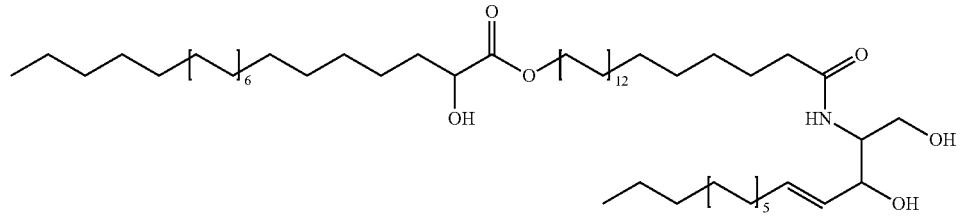

Ceramide 6 (Type I)

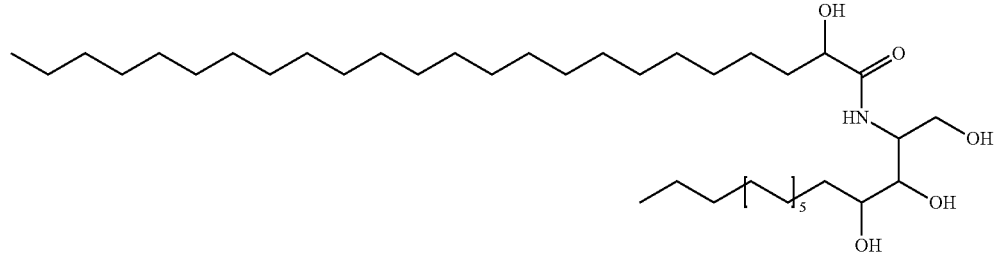

Ceramide 6 (Type II)

Preferably, the sphingolipid is ceramide 2 and/or ceramide 3.

The compositions of the present invention may further include one or more cosmetically acceptable additives, adjuvants, thickening agents, conditioning agents, and solvents. These cosmetically acceptable agents may be provided alone or in combination with one another to formulate a shampoo, conditioner, or shampoo-conditioner combination as required. Typically, such agents are present in the composition from about 0%-99.99% by weight, based on the total weight of the composition. Preferably, the composition contains from about 10%-90% by weight of such agents, such as for example from about 20% to about 80% by weight, based on the total weight of the composition.

In the present invention, "cosmetically acceptable additives" include, for example, monoalcohols, polyalcohols, glycol ethers, fatty acid esters, preserving agents, sequestering agents, softening agents, foaming agents, dyes, viscosity-modifying agents, nacreous agents, hydrating agents, antidandruff agents, antiseborrhoeic agents, sunscreen agents, surfactants, proteins, vitamins, α-hydroxy acids, salts, detoxifying agents, anti-inflammatory agents, fragrances, and combinations thereof.

Non-limiting examples of cosmetically acceptable adjuvants useful in the present invention include nonionic surface-active agents selected from polyethoxylated amides, polypropoxylated or polyglycerolated alcohols, α-diols, alkylphenols, and fatty acids having a fatty chain containing, for example, 8 to 18 carbon atoms.

Non-limiting examples of cosmetically acceptable thickening agents include sodium alginate, gum arabic, cellulose derivatives (such as methylcellulose, hydroxymethylcellulose, hydroxyethylcellulose, hydroxypropylcellulose and hydroxypropylmethylcellulose), guar gum or derivatives thereof, xanthan gums, scleroglucans, crosslinked polyacrylic acids, polyurethanes, copolymers based on maleic acid or on maleic anhydride, associative thickeners bearing fatty chains of natural or unnatural origin. Such thickening agents may also be obtained by mixing (i) polyethylene glycol and polyethylene glycol stearates or distearates or (ii) phosphoric esters and amides.

Non-limiting examples of cosmetically acceptable solvents include water, monoalcohols, polyalcohols, glycol ethers or fatty acid esters, which are used alone or as a mixture. For example, ethanol, isopropanol, polyalcohols such as ethylene glycol and diethylene glycol, glycol ethers, glycol alkyl ethers or diethylene glycol alkyl ethers may be used. Preferably, the cosmetically acceptable solvent is water.

Non-limiting examples of cosmetically acceptable conditioning agents include linear or branched (saturated or unsaturated) cyclic or aliphatic hydrocarbons (synthetic or non-synthetic), hydrogenated or unhydrogenated natural oils, soluble or insoluble volatile or non-volatile silicones (which, optionally, may be organically modified, fluorinated or perfluorinated oils), polybutenes and polyisobutenes, fatty esters in liquid, pasty or solid form, esters of polyhydric alcohols, glycerides, natural or synthetic waxes, silicone gums and resins, or mixtures of the foregoing.

The compositions of the present invention may be incorporated into separate shampoo and hair conditioner formulations or into combined shampoo and conditioner formulations.

In certain preferred embodiments, the invention is a shampoo or hair conditioner composition, which includes a lipid and creatine. In this embodiment, the lipid and creatine are each present in amounts of about 0.01% to about 10.0% by weight relative to the total weight of the composition. The shampoo and hair conditioner compositions of this embodiment include the same components in the same quantities as described above.

The compositions of the present invention may be produced using methods well-known in the art and as further described in the Examples below. The compositions may be produced in various forms, including, for example, a concentrated form, whereby the compositions are, preferably, diluted before use in an aqueous medium. Alternatively, the compositions may be formulated at concentrations that are ready for use without further dilution. The compositions may be formulated as creams, gels, or foams. Such compositions may be packaged and used in connection with, e.g., a pressurized container, a pump, or a squeeze container.

Typically, the pH of a composition of the present invention is between about 2 and about 9. Preferably, the pH of a composition of the present invention is between about 3 to about 8. The shampoo compositions of the present invention, preferably, have a pH between about 5 and about 6.5. The conditioner compositions of the present invention, preferably, have a pH between about 3 and about 5. The pH of the composition may be adjusted, if necessary, using cosmetically acceptable acids or bases, such as but not limited to citric acid and sodium hydroxide, respectively.

Another embodiment of the present invention is a method for improving the tensile properties of hair. This method includes applying to hair a composition that includes from about 0.01% to 10.0% by weight relative to the total weight of the composition of a lipid and from about 0.01% to 10.0% by weight relative to the total weight of the composition of creatine. In this method, the lipid is selected from ceramides, glucosylceramides, cholesterol, fatty acids ($C_{10}$-$C_{22}$) and combinations thereof. Preferably, the lipid is ceramide 2, ceramide 3, and/or cholesterol.

As used herein, "tensile properties" refers to the relative strength and elasticity of hair. In the present invention, various parameters may be used to evaluate the relative strength and elasticity of hair. One such parameter is tensile strength, which means the maximal force per unit cross-sectional area that hair can withstand until it breaks. Calculation of tensile strength is well within the skill of the art and may be accomplished using the appropriate apparatus, such as for example, a Dia-Stron MTT600 Auto Sampler (from Dia-Stron, Ltd., UK). Another parameter included within "tensile properties" is "break extension." As used herein, "break extension" means the percent extension from original length, before breakage, of hair. Break extension is calculated as follows: Length hair stretched when broken–Original Hair length/Original Hair length×100.

Yet another parameter included within "tensile properties" is the "work-to-break" value, which relates the amount of energy (in joules) required to break hair multiplied by the distance the hair is stretched. Work-to-break is calculated as follows: Work=Force×distance/cross-sectional area (or Grams force to break×distance hair is stretched/cross-sectional area).

Surprisingly and unexpectedly, hair that is treated with a composition according to the present invention, i.e., a composition containing a combination of a lipid and creatine, has improved tensile properties compared to hair treated with the same composition containing (a) neither a lipid nor creatine or (b) a composition containing a lipid or creatine, but not both.

In the present invention, hair has improved tensile properties if at least one parameter thereof is improved after treatment with one or more compositions of the present invention compared to treatment with a composition that does not contain a combination of a lipid and creatine, such as for example, ceramide 3 and creatine. Preferably, the improvement is manifested as an increase in break extension or work to break hair when lipids and creatine are combined compared to either ingredient alone.

In the present invention, a shampoo composition according to the present invention is applied to the hair and then worked into the hair manually. The hair is then optionally rinsed with water. Optionally, this shampoo step is repeated one or more times, such as one to three times. Thereafter, a conditioner composition according to the present invention may optionally be applied to the hair and worked into the hair. The conditioner is allowed to remain in the hair for about 0 to about 5 minutes and is then optionally rinsed out with water. Optionally, this hair conditioner conditioning step may be repeated one or more times, such as one to three times. In the present invention, "treatment" refers to applying a regime of shampoo and conditioner as defined herein in the manner described above. Alternatively, improved tensile properties may be achieved using either the shampoo or the conditioner (or a combination shampoo-conditioner) compositions of the present invention alone.

Another embodiment of the present invention is a hair treatment composition that is made by a process that includes combining from about 0.01% to about 10.0% by weight relative to the total weight of the composition of a lipid and from about 0.01% to about 10% by weight relative to the total weight of the composition of creatine to form the composition. Such a product may optionally contain one or more cosmetically acceptable additives, adjuvants, thickening agents, conditioning agents, and solvents as defined above.

The following examples are provided to further illustrate methods of preparation of the compositions of the present invention, as well as certain physical properties of these materials. These examples are illustrative only and are not intended to limit the scope of the invention in any way.

EXAMPLES

Example 1

Creatine And Ceramide Formulations

As used herein, "ALS" refers to ammonium lauryl sulfate; "cocamide MEA" refers to cocamide ethanolamines (a foam enhancing agent); "Kathon CG" (a preservative) refers to a commercially-available chemical that comprises a mixture of methylchloroisothiazolinone and methylisothiazolinone; "Mackconditioner Brite" refers to a commercially-available concentrated hair conditioner composition offered by the McIntyre Group Ltd. (University Park, Ill.); and "Fanning LIM-1" refers to a commercially-available dimethicone copolyol meadowfoamate composition offered by the Fanning Corporation (Chicago, Ill.). The following shampoo and conditioner formulations were prepared, as described below.

TABLE 1

Ceramide 3/Creatine Shampoo Formulas

| Ingredient | Creatine Wt % | Ceramide 3 Wt % | Creatine & Ceramide 3 Wt % |
|---|---|---|---|
| Deionized water | 61.95 | 60.95 | 59.95 |
| ALS | 25.00 | 25.00 | 25.00 |
| Cocoamidopropyl betaine | 10.00 | 10.00 | 10.00 |
| Cocamide MEA | 2.00 | 2.00 | 2.00 |
| Creatine | 1.00 | 0.00 | 1.00 |
| Ceramide 3 | 0.00 | 2.00 | 2.00 |
| Citric Acid | 0.02 | 0.02 | 0.02 |
| Kathon CG | 0.03 | 0.03 | 0.03 |
| Total | 100.00 | 100.00 | 100.00 |

The shampoos described in Table 1 were prepared by adding deionized water, ALS, and cocoamidopropyl betaine to a mixer with moderate agitation. Once the foregoing components were thoroughly mixed, the solution was heated to 160° F. Next, cocamide MEA was added and mixed until it melted. Ceramide 3 was then added. The solution was then cooled to 110° F. Creatine was then added to the solution and mixed. Finally, citric acid and Kathon CG were added and mixed.

TABLE 2

Ceramide 3/Creatine Conditioner formulas

| Ingredient | Creatine Wt % | Ceramide 3 Wt % | Creatine & Ceramide 3 Wt % |
|---|---|---|---|
| Fanning LIM-1 | 20.00 | 20.00 | 20.00 |
| Mackconditioner Brite | 4.0 | 4.0 | 4.0 |
| Deionized water | 74.97 | 73.97 | 72.97 |
| Creatine | 1.00 | 0.00 | 1.00 |
| Ceramide 3 | 0.00 | 2.00 | 2.00 |
| Kathon CG | 0.03 | 0.03 | 0.03 |
| | 100.00 | 100.00 | 100.00 |

The conditioner described in Table 2 was prepared by adding Fanning LIM-1 to a mixer with moderate agitation, which was then heated to 160° F. Next, Mackconditioner Brite was added and mixed until it melted. Ceramide 3 was then added. The solution was cooled to 110° F. Creatine was subsequently added and thoroughly mixed. Finally, Kathon CG was added and mixed.

Example 2

Hair Elasticity & Strength

The effect of the shampoo and conditioner formulations described in Example 1 on the tensile properties of hair was evaluated. Swatches of triple-bleached Caucasian hair, each about 7/8" in width, were treated with a shampoo followed by a conditioner according to Table 3 and as further described below.

TABLE 3

| Group | Description | Formulation |
|---|---|---|
| I | Ceramide 3 (2%) shampoo | Table 1 |
| | Ceramide 3 (2%) conditioner | Table 2 |
| II | Creatine (1%) shampoo | Table 1 |
| | Creatine (1%) conditioner | Table 2 |
| III | Creatine (1%) + Ceramide 3 (2%) shampoo | Table 1 |
| | Creatine (1%) + Ceramide 3 (2%) conditioner | Table 2 |

In this example, each swatch of hair was first rinsed in deionized water. Next, the hair was washed with 4-6 grams of a shampoo from Group I, II, or III for 1 minute. The hair was then rinsed 10 times in 500 mL of fresh deionized water. The foregoing wash and rinse step was repeated twice. Next, each swatch of hair was massaged in the corresponding conditioner, i.e., from Group I, II, or III, for 1 minute. The hair was allowed to sit in such conditioner for 3 minutes. Next, the hair was rinsed 10 times in 500 mL of deionized water The hair was allowed to dry overnight. The different groups of hair swatches were placed in a climate controlled chamber set at 25° C., 65% relative humidity environment for 24 hours.

The cross-sectional area of the hair swatches was measured using a Mitutoyo LSM 3100 (and returned to the climate controlled chamber for at least 2 hours). Next, a tensile test was performed on the hair swatches using a Dia-Stron MTT600 Auto Sampler (UK). The tensile test measured elasticity of each test group of hair. Specifically, each hair swatch was stretched until it failed (i.e., broke). The percentage of hair extension at which breakage was observed was determined for each swatch of hair (referred to herein as the "Break Extension" value). In addition, the amount of force required to break each swatch of hair (per unit of cross-sectional area) was evaluated. The relative force values (and cross-sectional areas for each swatch of hair) were used to calculate the amount of work required to break each swatch of hair. All data were analyzed using Statgraphics Version 2.0 software.

The hair swatches treated with shampoos and conditioners containing ceramide 3 alone (Group I) or creatine alone (Group II) yielded a smaller Break Extension value than the swatch treated with a shampoo and conditioner containing both ceramide 3 and creatine (Group III). Accordingly, the combination of such lipid and creatine imparted enhanced tensile (elasticity) properties on such hair, namely, it increased the relative Break Extension value. FIG. 1 shows the synergistic effect that the combination of ceramide 3 and creatine has on hair elasticity properties (as noted at the top of the triangle formed by the 3 data points).

Figure 2:
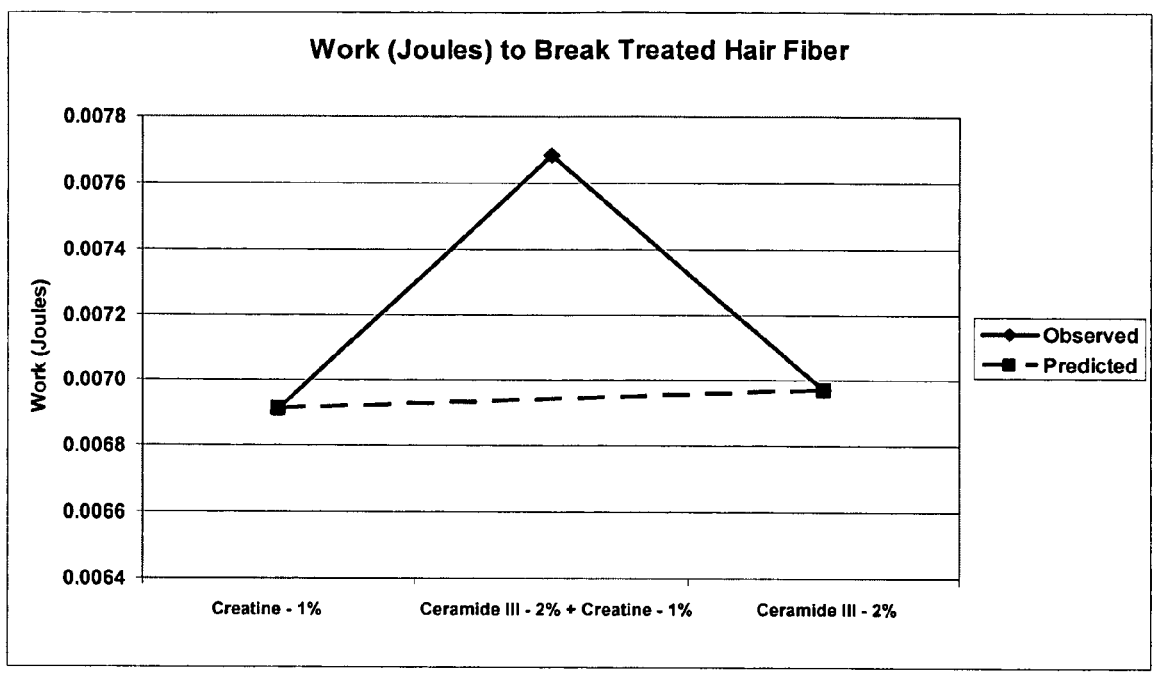
FIG. 2 is a line graph showing that hair treated with shampoo/conditioner formulations having both ceramide 3 and creatine has improved tensile strength (compared to predicted values).

The hair swatches treated with shampoos and conditioners containing ceramide 3 alone (Group I) or creatine alone (Group II) required less work to break than the swatch of hair treated with a shampoo and conditioner containing both ceramide 3 and creatine (Group III). Accordingly, the combination of such lipid and creatine imparted enhanced tensile (strength) properties on such hair, namely, it increased the amount of work required to break the hair. FIG. 2 further shows the synergistic effect that the combination of ceramide 3 and creatine has on hair strength (as noted at the top of the triangle formed by the 3 data points).

The data for such tensile property tests are summarized in Table 4 below.

TABLE 4

| Group | n | Break Extension (%) | Total Work (Joules) |
|---|---|---|---|
| I | 99 | 52.8675 | 0.00696952 |
| II | 94 | 51.4330 | 0.00691266 |
| III | 83 | 53.1350 | 0.00768530 |

Example 3

Creatine and Cholesterol Formulations

The following example further demonstrates the synergistic effects provided by the hair treatment compositions of the present invention. In this example, three test shampoos and conditioners were formulated. A shampoo and conditioner included 2% (wt) creatine (but no cholesterol), and were produced as described above with respect to the compositions described in Tables 1 and 2. A second shampoo and conditioner included 2% (wt) cholesterol (but no creatine), and were produced as described above with respect to the compositions described in Tables 1 and 2, with the exception that ceramide 3 was replaced with cholesterol.

A third shampoo and conditioner included 1% (wt) creatine and 1% (wt) cholesterol, and were produced as described above with respect to the compositions described in Tables 1 and 2, with the exception that ceramide 3 (2%) was replaced with cholesterol (1%). The shampoo and conditioner formulations used in this example are set forth below in Tables 5 and 6, respectively.

TABLE 5

Shampoo formulas for Cholesterol/Creatine Study

| Ingredient | Creatine Wt % | Cholesterol Wt % | Creatine & Cholesterol Wt % |
|---|---|---|---|
| Deionized water | 60.95 | 60.95 | 60.95 |
| ALS | 25.00 | 25.00 | 25.00 |
| Cocoamidopropyl betaine | 10.00 | 10.00 | 10.00 |
| Cocamide MEA | 2.00 | 2.00 | 2.00 |
| Creatine | 2.00 | 0.00 | 1.00 |
| Cholesterol | 0.00 | 2.00 | 1.00 |
| Citric Acid | 0.02 | 0.02 | 0.02 |
| Kathon CG | 0.03 | 0.03 | 0.03 |
| Total | 100.00 | 100.00 | 100.00 |

TABLE 6

Conditioner formulas for Cholesterol/Creatine Study

| Ingredient | Creatine Wt % | Cholesterol Wt % | Creatine and Cholesterol Wt % |
|---|---|---|---|
| Fanning LIM-1 | 20.0 | 20.0 | 20.0 |
| Mackconditioner Brite | 4.00 | 4.00 | 4.00 |
| Deionized water | 73.97 | 73.97 | 73.97 |
| Creatine | 2.00 | 0.00 | 1.00 |
| Cholesterol | 0.00 | 2.00 | 1.00 |
| Kathon CG | 0.03 | 0.03 | 0.03 |
| | 100.00 | 100.00 | 100.00 |

The shampoo and conditioner formulations were applied to three groups of triple-bleached Caucasian hair swatches, in accordance with Table 7 below.

TABLE 7

| Group | Description | Formulation |
|---|---|---|
| I | Creatine (2%) shampoo | Table 5 |
|   | Creatine (2%) conditioner | Table 6 |
| II | Cholesterol (2%) shampoo | Table 5 |
|   | Cholesterol (2%) conditioner | Table 6 |
| III | Creatine (1%) + Cholesterol (1%) shampoo | Table 5 |
|   | Creatine (1%) + Cholesterol (1%) conditioner | Table 6 |

The formulations were applied to such hair using the process described in Example 2, with the exception that the hair was treated an additional 4 times.

Figure 3:
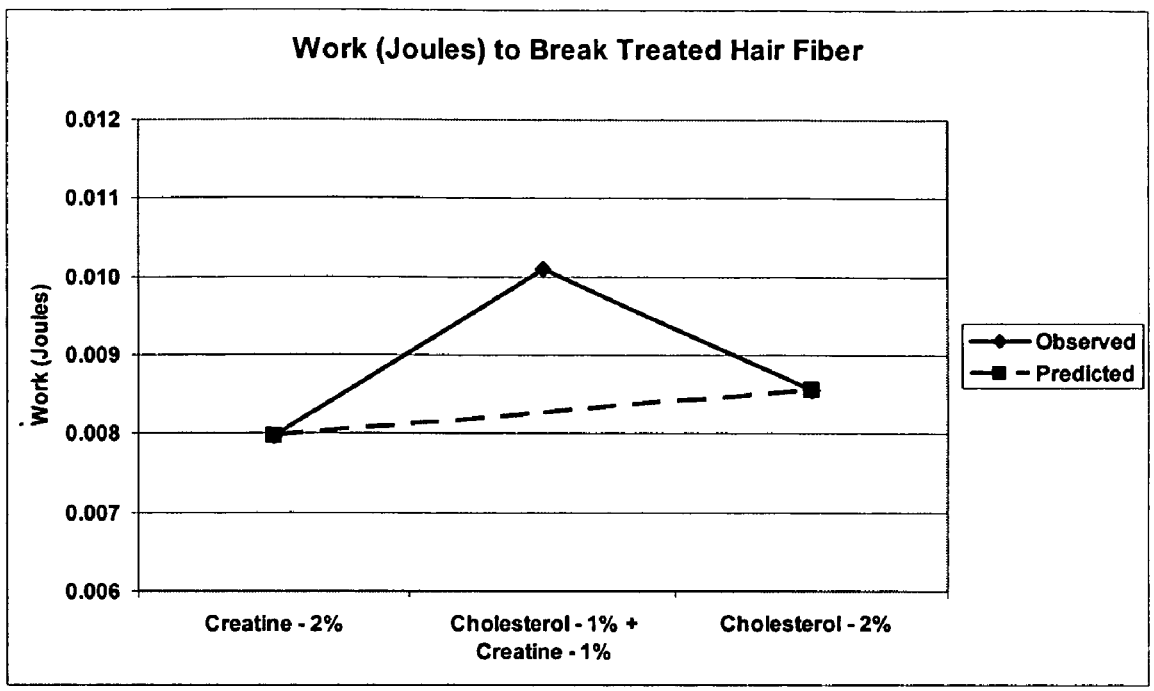
FIG. 3 is a line graph showing that hair treated with shampoo/conditioner formulations having 1% creatine and 1% cholesterol (Group III) has improved tensile strength values compared to predicted values—which are based on tensile strength values provided by the same shampoo/conditioner formulations that contained 2% creatine, but no cholesterol (Group I), and 2% cholesterol, but no creatine (Group II).
Figure 4:
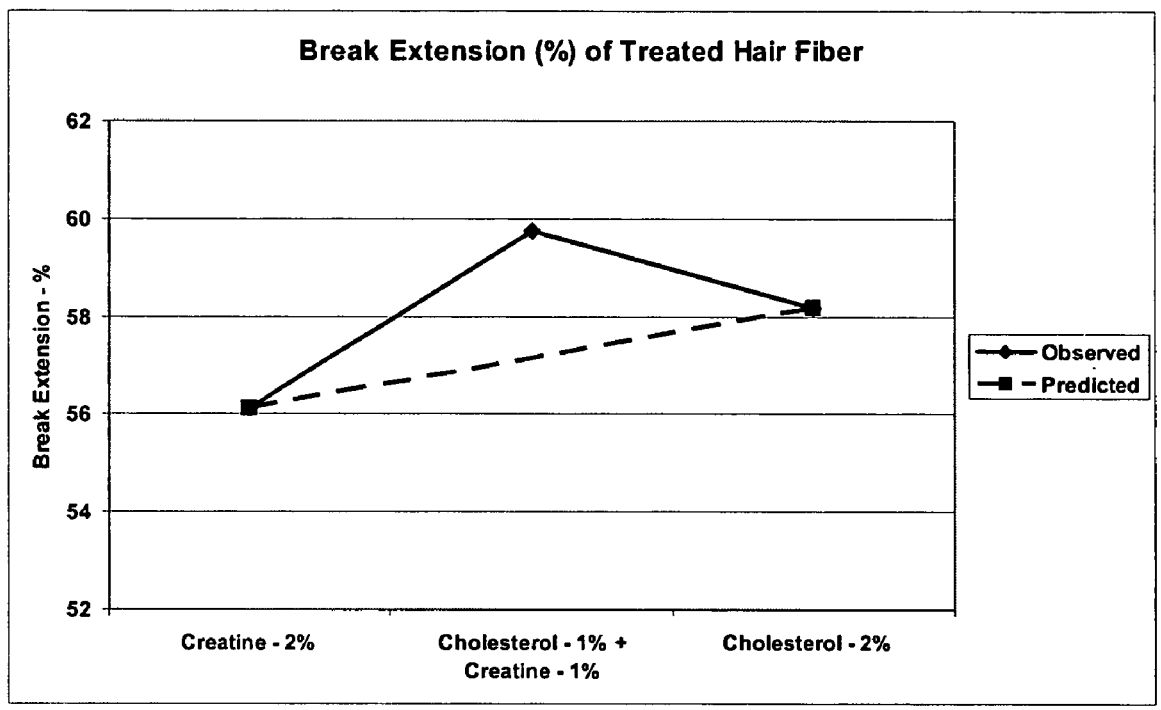
FIG. 4 is a line graph showing that hair treated with shampoo/conditioner formulations having 1% creatine and 1% cholesterol has superior Break Extension values (compared to predicted values).

The tensile properties of the treated hair were subsequently evaluated, as described in Example 2. The hair treated with shampoo (and conditioner) comprising 1% creatine and 1% cholesterol required more work to break than hair treated with formulations comprising 2% creatine or 2% cholesterol alone. Such data are summarized in Table 8 below. FIGS. 3 and 4 further demonstrate the hair strength and elasticity benefits that the compositions of the present invention provide.

TABLE 8

| Group | n | Break Extension (%) | Total Work (Joules) |
|---|---|---|---|
| I | 94 | 56.124 | 0.00796844 |
| II | 99 | 58.194 | 0.0085484 |
| III | 83 | 59.740 | 0.01010 |

Accordingly, this example further demonstrates the synergistic effects of hair treatment compositions comprising lipids and creatine on the tensile properties of hair.

Example 4

Creatine and Lipid Blend Formulations

A hair treatment composition including a combination of various lipids, along with creatine, was evaluated in this example. In addition, this example demonstrates the synergistic effects that such lipid and creatine compositions provide at lower concentrations. The lipid blend formula set forth in Table 9 below was used in this example.

TABLE 9

| Ingredient | Wt % |
| --- | --- |
| Meadowfoam Seed Oil | 75.00 |
| Behenic Acid | 3.375 |
| Cholesterol | 3.375 |
| Ceramide 3 | 4.5 |
| Ceramide 2 | 1.25 |
| Bishydroxyethyl Biscetyl Malonamide (Questamide H) | 12.5 |
| Total | 100.00 |

This lipid blend, along with creatine, was incorporated into the shampoo and conditioner formulas set forth in Tables 10 and 11, respectively. The shampoos and conditioners were produced as described above with respect to the compositions described in Tables 1 and 2, respectively.

TABLE 10

Creatine/Lipid Blend Shampoo Formulas

| Ingredient | Creatine Wt % | Lipid Blend Wt % | Creatine & Lipid Blend Wt % |
| --- | --- | --- | --- |
| Deionized water | 62.85 | 62.85 | 62.85 |
| ALS | 25.00 | 25.00 | 25.00 |
| Cocoamidopropyl betaine | 10.00 | 10.00 | 10.00 |
| Cocamide MEA | 2.00 | 2.00 | 2.00 |
| Creatine | 0.10 | 0.00 | 0.05 |
| Lipid Blend | 0.00 | 0.10 | 0.05 |
| Citric Acid | 0.02 | 0.02 | 0.02 |
| Kathon CG | 0.03 | 0.03 | 0.03 |
| Total | 100.00 | 100.00 | 100.00 |

TABLE 11

Creatine/Lipid Blend Conditioner Formulas

| Ingredient | Creatine Wt % | Lipid Blend Wt % | Creatine & Lipid Blend Wt % |
| --- | --- | --- | --- |
| Fanning LIM-1 | 20.0 | 20.0 | 20.0 |
| Mackconditioner Brite | 4.00 | 4.00 | 4.00 |
| Deionized water | 75.87 | 75.87 | 75.87 |
| Creatine | 0.10 | 0.00 | 0.05 |
| Lipid Blend | 0.00 | 0.10 | 0.05 |
| Kathon CG | 0.03 | 0.03 | 0.03 |
|  | 100.00 | 100.00 | 100.00 |

Figure 5:
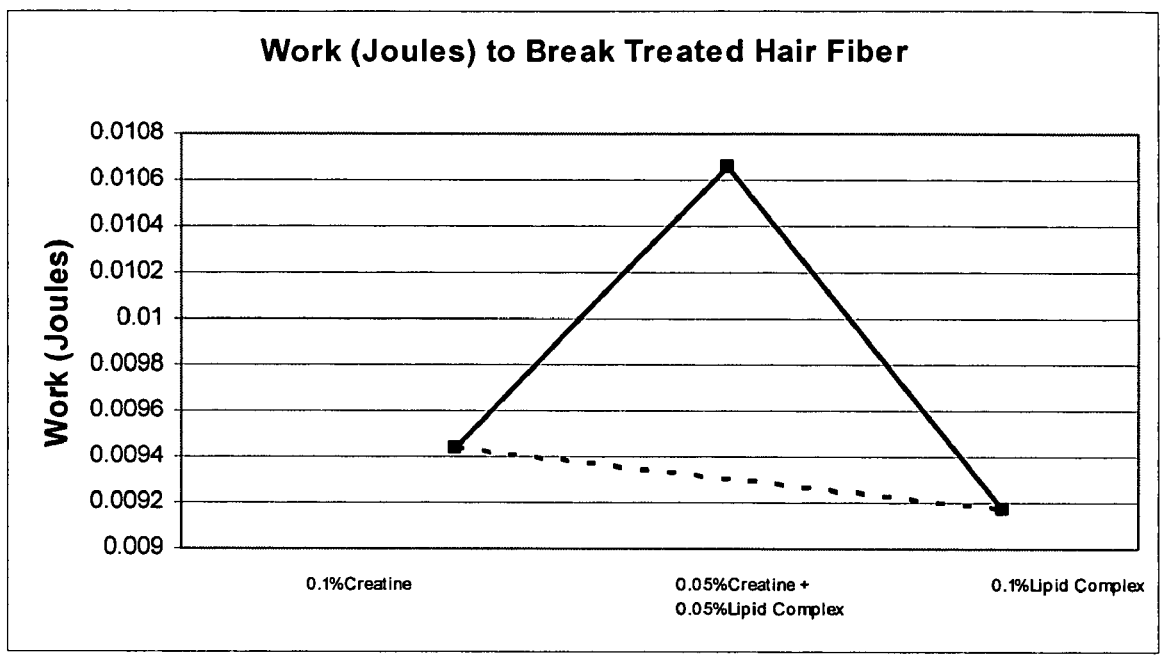
FIG. 5 is a line graph showing that hair treated with shampoo/conditioner formulations having 0.05% creatine and 0.05% of a lipid blend (described in Example 5 below) has improved tensile strength values compared to predicted values—which are based on tensile strength values provided by the same shampoo/conditioner formulations that contained 0.1% creatine, but no lipid blend, and 0.1% lipid blend, but no creatine.

These shampoos and conditioners were applied to hair using the process described in Example 2. Following application of these test shampoos and conditioners, the tensile properties of the treated hair were subsequently evaluated, as described in Example 2. The hair treated with shampoo (and conditioner) comprising 0.05% creatine and 0.05% lipid blend required more work to break than hair treated with formulations comprising 0.1% creatine or 0.1% lipid blend alone. Such data are summarized in Table 12 below and FIG. 5.

TABLE 12

| Group | n | Total Work (Joules) |
| --- | --- | --- |
| Creatine Alone | 46 | 0.00944 |
| Lipid Blend Alone | 46 | 0.00917 |
| Creatine + Lipid Blend | 41 | 0.01066 |

This example further illustrates the hair strength and elasticity benefits that the compositions of the present invention provide, and, in particular, the synergistic effects that even low levels of such lipid blend/creatine combinations will have on hair tensile properties.

Although illustrative embodiments of the present invention have been described herein, it should be understood that the invention is not limited to those described, and that various other changes or modifications may be made by one skilled in the art without departing from the scope or spirit of the invention.

What is claimed is:

1. A hair treatment composition formulated as a shampoo, a conditioner, or combinations thereof, wherein the composition comprises (i) 1% creatine and 1% lipid; (ii) 1% creatine and 2% lipid; or (iii) 0.05% creatine and 0.05% lipid, by weight relative to the total weight of the composition.

2. A composition according to claim 1, further comprising free amino acids other than creatine.

3. A composition according to claim 2, wherein the free amino acids are naturally occurring, non-naturally occurring, or combinations thereof.

4. A composition according to claim 1, wherein the lipid is ceramide 3, cholesterol, or a lipid blend comprising ceramide 3 and cholesterol.

5. A hair treatment composition made by a process, which comprises combining (i) 1% creatine and 1% lipid; (ii) 1% creatine and 2% lipid; or (iii) 0.05% creatine and 0.05% lipid, by weight relative to the total weight of the composition to form the composition, wherein the hair treatment composition is formulated as a shampoo, a conditioner, or combinations thereof.

6. A composition according to claim 1, wherein the composition further comprises one or more of a cosmetically acceptable additive, a cosmetically acceptable adjuvant, a cosmetically acceptable thickening agent, a cosmetically acceptable conditioning agent, and a cosmetically acceptable solvent.

7. A composition according to claim 6, wherein the cosmetically acceptable additive is selected from the group consisting of monoalcohols, polyalcohols, glycol ethers, fatty acid esters, preserving agents, sequestering agents, softening agents, foaming agents, dyes, viscosity-modifying agents, nacreous agents, hydrating agents, anti-dandruff agents, anti-seborrhoeic agents, sunscreen agents, surfactants, proteins, vitamins, α-hydroxy acids, detoxifying agents, fragrances, salts thereof, and combinations thereof.

8. A composition according to claim 6, wherein the cosmetically acceptable adjuvant is a nonionic surface active agent.

9. A composition according to claim 1, wherein the composition further comprises from about 25% to about 37% surfactant by weight relative to the total weight of the composition.

* * * * *